(12) United States Patent
Berger et al.

(10) Patent No.: US 6,576,125 B2
(45) Date of Patent: Jun. 10, 2003

(54) METHOD OF SAMPLE INTRODUCTION FOR CHROMATOGRAPHIC SYSTEMS

(75) Inventors: Terry A. Berger, Newark, DE (US); Kimber D. Fogelman, Hockessin, DE (US)

(73) Assignee: Berger Instruments, Inc., Newark, DE (US)

( * ) Notice: Subject to any disclaimer, the term of this patent is extended or adjusted under 35 U.S.C. 154(b) by 64 days.

(21) Appl. No.: 09/931,238

(22) Filed: Aug. 17, 2001

(65) Prior Publication Data

US 2003/0034307 A1 Feb. 20, 2003

(51) Int. Cl.[7] .............................................. B01D 15/08
(52) U.S. Cl. ..................... 210/198.2; 210/656; 210/659
(58) Field of Search ................................ 210/635, 656, 210/659, 198.2, 634; 95/82, 89; 96/101, 105; 422/70

(56) References Cited

U.S. PATENT DOCUMENTS

| | | | | |
|---|---|---|---|---|
| 4,871,453 A | * | 10/1989 | Kumar | 210/198.2 |
| 5,013,443 A | * | 5/1991 | Higashidate | 210/634 |
| 5,180,487 A | * | 1/1993 | Saito | 210/198.2 |
| 5,322,627 A | * | 6/1994 | Berger | 210/656 |
| 5,340,476 A | * | 8/1994 | Berger | 210/198.2 |
| 5,346,622 A | * | 9/1994 | Klee | 210/659 |
| 5,360,320 A | * | 11/1994 | Jameson | 417/4 |
| 5,458,783 A | * | 10/1995 | Levy | 210/659 |
| 6,428,702 B1 | * | 8/2002 | Berger | 210/634 |

* cited by examiner

*Primary Examiner*—Ernest G. Therkorn
(74) *Attorney, Agent, or Firm*—Zito tlp; Joseph J. Zito

(57) ABSTRACT

An improved method of introducing sample into a low-pressure flow stream of a high-pressure chromatography system to improve efficiency and significantly shorten the time of the separation process through a chromatography column is described. The method comprises injecting samples in a modifier liquid flow stream upstream of a mixing column that combines two independent flow streams of a liquid modifier with a highly compressed solvating fluid. Focusing can be controlled at the column head by changing the ratios of the two flow streams. Total flow may also be adjusted to speed the application of the sample onto the column during injection. The method improves the timing and efficiency of a supercritical fluid chromatography system and can reduce the amount of modifier added to the mobile phase flow stream.

15 Claims, 2 Drawing Sheets

METHOD OF SAMPLE INTRODUCTION FOR CHROMATOGRAPHIC SYSTEMS

BACKGROUND OF THE INVENTION

A separation technology called supercritical fluid chromatography (SFC) has advanced over the past decade. SFC uses highly compressible mobile phases, which typically employ carbon dioxide ($CO_2$) as a principle component. In addition to $CO_2$, the mobile phase frequently contains an organic solvent modifier, which adjusts the polarity of the mobile phase for optimum chromatographic performance. A common gradient range for gradient SFC methods might occur in the range of 2% to 60% composition of the organic modifier. Since different components of a sample may require different levels of organic modifier to elute rapidly, a common technique is to continuously vary the mobile phase composition by linearly increasing the organic modifier content. This technique is called gradient elution. SFC instruments, while designed to operate in regions of temperature and pressure above the critical point of carbon dioxide ($CO_2$), are typically not restricted from operation well below the critical point. In this lower region, especially when organic modifiers are used, chromatographic behavior remains superior to traditional HPLC and often cannot be distinguished from true supercritical operation.

SFC has been proven to have superior speed and resolving power compared to traditional methods, such as high-performance liquid chromatography (HPLC) for analytical applications. This results from the dramatically improved diffusion rates of solutes in SFC mobile phases compared to other analytical methods, such as HPLC mobile phases. Separations have been accomplished as much as an order of magnitude faster using SFC instruments compared to HPLC instruments using the same chromatographic column. A key factor to optimizing SFC separations is the ability to independently control flow, density and composition of the mobile phase over the course of the separation. SFC instruments used with gradient elution also re-equilibrate much more rapidly than corresponding HPLC systems. As a result, they are ready for processing a consecutive sample after a shorter period of time.

Analysts have several objectives in employing preparative elution chromatography. First, they wish to achieve the highest available purity of each component of interest. Second, they wish to recover the maximum amount of the components of interest. Third, they wish to process sequential, possibly unrelated samples as quickly as possible and without contamination from prior samples. Finally, it is frequently desirable to recover samples in a form that is rapidly convertible either to the pure, solvent-free component or to a solution of known composition which may or may not include the original collection solvent.

SFC systems operate with varying compositions of two independently controlled flow streams: the first flow stream delivers a highly compressed fluid, such as carbon dioxide, and a second stream delivers a modifier solvent, such as methanol. The two independent flow streams are combined into a single flow stream that enters the separation column. In both HPLC and SFC, sample is normally introduced into the flow stream by means of an injection valve. Common injection valves are fixed-loop multi-port injection valves with either internal or external loops. Direct full loop injections are normal means of sample introduction in SFC so that a packed column has similar quantitative reproducibility to LC using fixed-loop injectors. Injection valves used in SFC sample introduction present special hazards caused by the higher pressures (up to 600 bar) found in SFC systems. Sample may be manually injected into the sample loop with a syringe through a fill port.

In SFC systems, the mobile phase is typically a mixture of an organic modifier and a highly compressed fluid, such as carbon dioxide ($CO_2$) delivered by two independent pumps. In the prior art, samples are dissolved in an organic solvent and then injected into the mobile phase stream at a location 21 just prior to entering a separation column. A problem with this method is that the organic modifier is typically the strongest solvent in the system and can cause uncontrolled elution of the sample components well into the bed of the separation column before the controlled process of gradient elution becomes effective. In this configuration, the liquid phase sample may never completely mix with the mobile phase in the SFC flow stream, thereby causing a concentrated, separated slug of sample to enter a separation column and cause smearing, high background noise, or varying separation times. The resultant component peaks will experience substantial broadening, producing poor chromatographic results. Particularly, the problem occurs with poorly retained components, which experience the greatest degree of broadening and are typically the most difficult to separate. The problems with broadening of peaks becomes severely and multiplied when larger sample volumes are used to apply the sample components to the column 26.

At least one prior art system has been built to inject samples into the modifier flow stream prior to mixing with the compressible fluid ($CO_2$) high-pressure flow stream in an SFC system is from Prochrom International, Champigneulles, France. The system is designed for sample injection for SFC into the modifier stream that uses a pump to continuously circulate sample in an external flow path having a plurality of control valves to control flow direction. Such a system has up to eight control valves that are manipulated to direct the sample into the flow stream. The pump circulates sample from a reservoir until flow loop contents are ready for injection into the low pressure flow stream. To inject, valves are closed to the reservoir and circulation pump and other valves are opened to the flow stream, thereby injecting the sample volume by flushing out the sample through the flow path containing sample with the moving flow stream. After injection, valves to the flow stream are closed and valves to the circulation pump are re-opened.

A few of the draw backs associated with the Prochrom configuration are that a pump must continually pump sample through a looping flow path and that a plurality of valves must be manually or automatically manipulated to make an injection. This time-consuming method is not amenable to the rapid repeated injections available in SFC and also add to complication and inaccuracies of injection. Also, since sample is continuously pumped through the flow loop prior to injection, partial loop injections are not possible. After injection, part of the flow path containing sample can become filled with flow stream contents, which in turn is circulated into the sample reservoir by the pump, thereby diluting the sample reservoir and subsequent sample injections to an unknown degree.

There is a need for efficient premixing samples with the actual mobile phase, prior to injection, to apply samples to a separation column in supercritical fluid chromatography or high performance liquid chromatography. A method for injection must be timely and not bottleneck a rapid injection, separation, and collection process in an SFC system. The method should control how the sample is delivered to the separation column. Finally, a method for premixing should be environmentally friendly and generate as little hazardous chemicals for disposal as possible and prevent hazardous chemicals from escaping into the atmosphere.

SUMMARY OF THE INVENTION

The invention is a method for introducing sample into the flow stream of chromatography systems that operate at high pressures, such as high-performance liquid chromatography (HPLC) or supercritical fluid chromatography (SFC), and mix two separate flow streams to create a single mobile phase flow stream. The method of the preferred embodiment is an improvement to high-pressure chromatography systems by introducing samples into a low-pressure modifier flow stream at a point prior to mixing with a high-pressure compressible fluid flow stream.

The present invention uses a multi-port injection valve with a sample injection loop to inject into the modifier flow stream. A syringe or syringe pump adds sample into the loop between injections. No additional valves or circulating pumps are necessary. Partial-loop injections into the flow stream are also possible. Because of the precise nature of the injections and no continual circulation of the sample into and out of a sample flow stream, the possibility of dilution of an injected sample is minimal. Virtually all of the sample injected into the modifier flow stream reaches the separation column.

The preferred method provides greater control over the SFC process by providing for pre-mixing of sample into a low-pressure flow stream and balancing of high-pressure compressible and low pressure incompressible flow streams to enhance the speed of separation and quality of chromatographic results. Focusing of sample components at the column head is also controlled by changing the ratio of compressible to incompressible flow streams.

The present invention addresses safety and time delay problems caused by injections of sample into high-pressure mobile phase flow streams. A sample injection valve in SFC introduces a measured sample into the mobile phase flow stream prior to entering a chromatography column. During an injection, the valve loop discharges sample contents into a mobile phase flow stream. After injection, high-pressure mobile phase becomes trapped inside the sample loop when the valve is returned to a load position. Setting the injection valve sample loop back to a load position also exposes the sample loop that is under high pressure to atmospheric pressure inside the laboratory. Compressed mobile phase in SFC will rapidly expand approximately 500 times when exposed to atmospheric pressure. A hazardous condition occurs when mobile phase trapped in an injection loop explodes out of the system through a sample fill port connected to the loop, and out into open air. Also, by moving the injection location to a low-pressure flow stream, blow-back of high-pressure mobile phase from an injection loop is avoided.

Dissipating pressure from a sample loop to a waste line causes delays to the injection process which slows the entire SFC sample processing time. The injection valve location that is positioned upstream of the mixing point for the incompressible and compressible (or supercritical) fluid flow streams removes the time-delays associated with dissipating pressures trapped in an injection valve and blow-back from an injection valve into a laboratory. The modifier flow stream at this location has lower pressure. Therefore, time delays caused by waiting for dissipation of a pressure-charged injection valves are avoided.

DETAILED DESCRIPTION OF A PREFERRED EMBODIMENT

Figure 1:
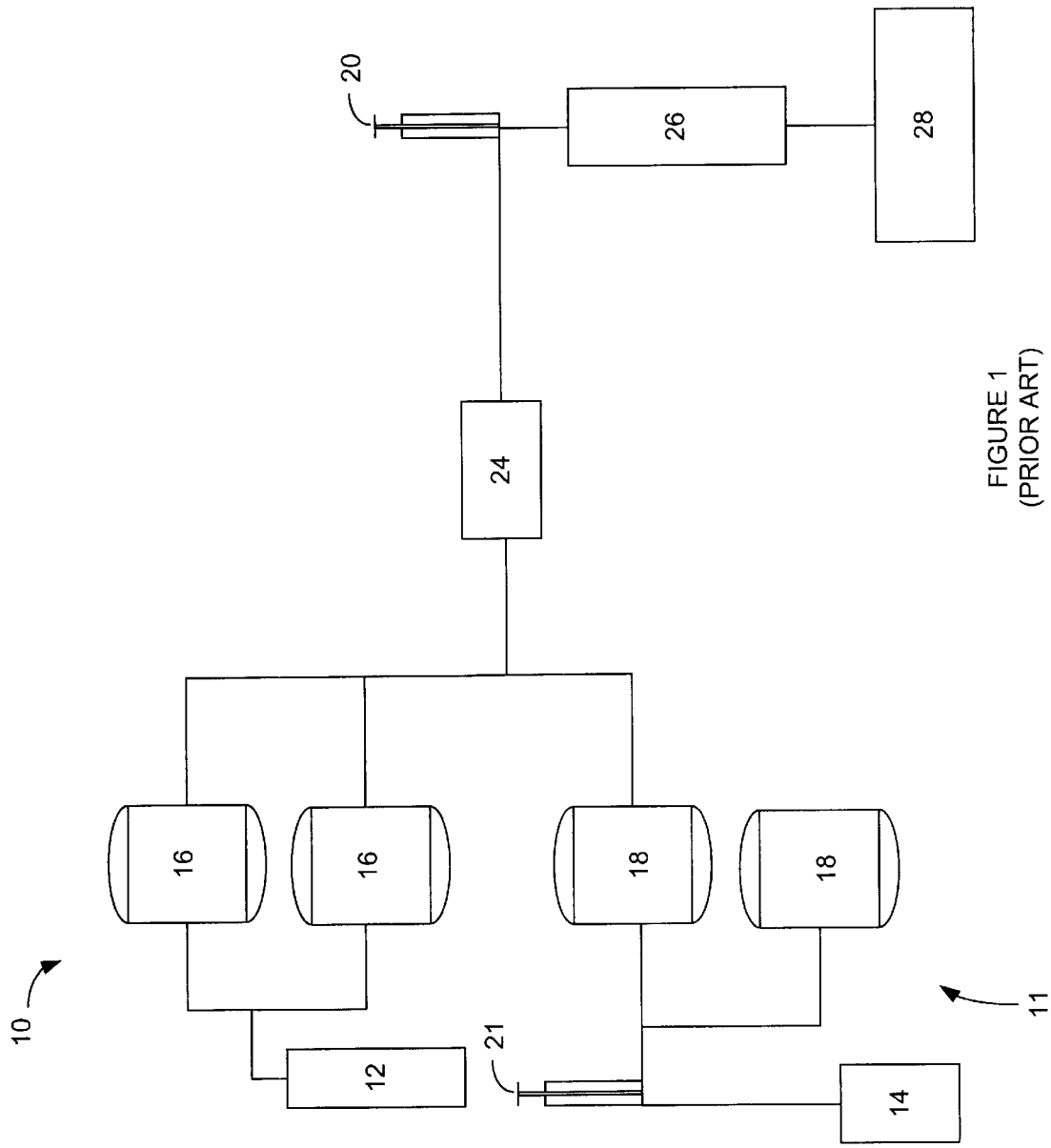
FIG. 1 illustrates a prior art SFC system.

A simplified example diagram of an SFC system in the prior art is illustrated in FIG. 1. The system has a first flow stream 10 containing a mixture of highly compressed fluid, compressible liquid or supercritical fluid. The flow stream supplies liquefied compressed carbon dioxide ($CO_2$) from a fluid supply tank 12. The $CO_2$ is drawn by two supercritical fluid pumps 16 that deliver high-pressure fluid at or near supercritical levels to mixing column 24.

A second supply stream 11 adds a relatively incompressible liquid to the system as a modifier to the first flow stream. Methanol is a common fluid to add as a modifier solvent into an SFC system, although other modifiers are used depending on the sample to be separated. Modifier is drawn from a supply tank 14 by one or more pumps 18. The modifier flow stream 11 and $CO_2$ flow stream 10 are combined together and enter a mixing column 24. The resultant combination is a mixture of modifier dissolved into the gaseous fluid that is at or near supercritical state. For a better understanding of the present invention, a more detailed explanation of the problems in SFC injections follows.

Injection valve 20 in traditional chromatography systems is located downstream of mixing column 24 and upstream of chromatography column 26. The valve 20 is typically placed upstream of the chromatography column 26 to mix the sample with the combined flow streams prior to entering column 24. The sample to be separated and analyzed is manually introduced by syringe into an injection valve 20, such as a fixed-loop injector, that injects the sample of interest into the flow stream. After separation of the sample occurs in the column 26, the elution mixture passes from the column outlet into a detector 28.

FIG. 1 illustrates an injection location 20 used in the prior art where the sample is premixed with liquid phase modifier prior to entering pump 18. This method can also produce erroneous separation results on the column and is not a workable solution in SFC. If sample is added to methanol, it will weaken the solvent modifier prior to pressurization of the flow stream. Adding sample during movement of modifier with pumps 18 also creates a pumping problem. The varying composition of the sample and combination of sample with modifier are difficult to define for matters of compressibility compensation and pump rate consistency required for precision pumping in SFC. For example, if the sample is a compressible fluid, the pump will also need dynamic compressibility compensation for a binary fluid of compressible and non-compressible fluids. This is a difficult and unnecessary step to perform. In addition, the sample is subjected to physical forces within the pump, which may produce undesirable consequences for sample compositions and mixtures and cross-contamination problems through a pump and associated transfer lines and valves between sample injections.

Figure 2:
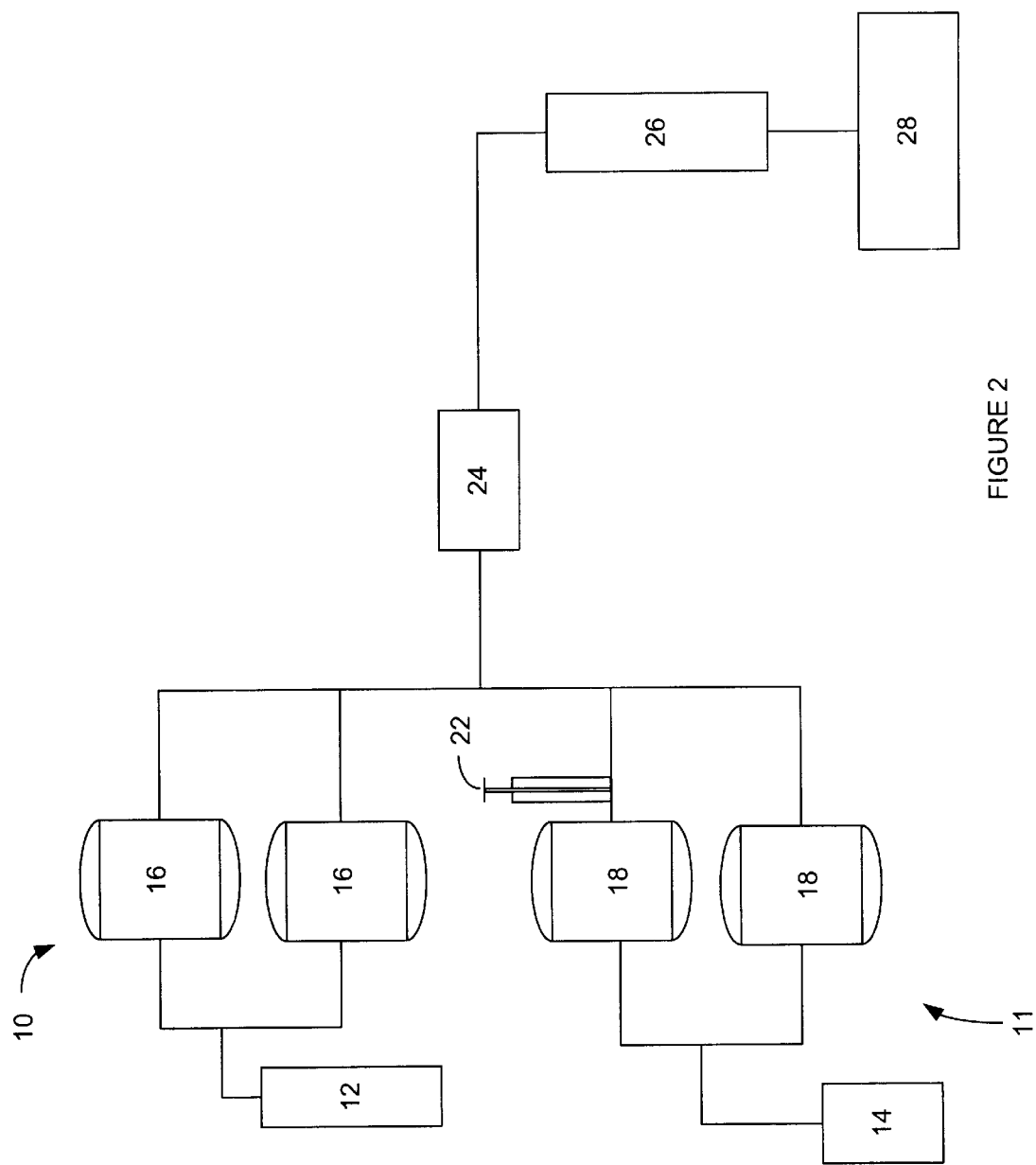
FIG. 2 illustrates an SFC system of the present invention

Referral is made to FIG. 2, illustrating a change of the injection valve 20 to a location 22 into the modifier flow stream downstream of pump 18, but upstream of mixing column 24. In this method, samples enter a low-pressure flow stream and become premixed with the high-pressure compressible fluid flow stream prior to entering the column 26. The invention is an improvement over the prior art by controlling focusing of retained sample components at the entrance to a chromatography column 26. The method also prevents uncontrolled elution of sample components into the bed of the separation column 26 before the controlled process of gradient elution becomes effective. The present invention uses a single multi-port injection valve with an injection loop to accomplish sample injection in the low-pressure flow stream. A syringe pump may be substituted for manually injecting sample into the valve between injections. No additional valves or circulating pumps are necessary. Partial-loop injections are also possible. Because of the precise nature of sample injection valves using a microliter sample loop, the possibility of dilution of sample from mixing with mobile phase is eliminated. Barring other system failures, virtually all of the sample injected into the chromatography system reaches the separation column 26.

The time of sample separation can be decreased by artificially increasing the composition of the modifier solvent, methanol, for some period. The time of separation can be increased by increasing the amount of carbon dioxide in the flow stream, which dilutes the methanol and sends methanol to the column in a weaker state for better retention of sample and modifier. For example, CO2 concentration can be doubled while leaving modifier concentration the same, creating a weaker solvent. The mobile phase may be a weaker concentration but carry the same amount of sample, which speeds up the application of elution liquid onto a column. The result is an improvement in the efficiency of an SFC system by speeding the time of sample through a column while contemporaneously achieving better chromatography results.

The method of the present invention results in greater control over compositional changes of the total flow stream during the injection period for better sample analysis and preparative production. Adding samples into the modifier flow stream 11 and mixing samples, modifier, and CO2 stream prior to application to the column provides greater control over sample focusing at the column head, which produces sharper peaks and better sample constituent detection. The technique allows the composition of the mobile phase to be carefully controlled at the time of injection to provide for a wide range of focusing and broadening conditions suitable for each particular set of components. For example, it would be desirable to broaden sample peaks where focusing might result in saturation of the components at the column head, leading to precipitation of certain components due to high column loading. The total flow rate may also be adjusted to speed the application of the sample onto the column 26 after injection. The flow rate may then be reduced to optimize the gradient separation.

The present invention also solves safety and efficiency problems caused by injections of samples into the high-pressure compressible SFC flow stream. An injection valve 22 works by receiving a measured volume of sample injected into a sample fill port either manually by a syringe or automatically with a syringe pump. To load the injection valve 22, a syringe is passed through a septum in a fill port and injects sample through the sample port, into the injection valve sample loop. The sample loop is partially or completely fill with sample, depending on volume. Overflow or displaced fluid from the sample loop exits the injection valve into a waste collection line. Through the fill port, the sample liquid enters into a sample loop that may partially or completely fill with sample. When sample is added to a sample loop of an injection valve, the sample liquid inside the loop is at atmospheric pressure. When the sample is ready for injection, the sample in the loop, at low pressure, is brought inline with the mobile phase that is a high pressure flow stream. The high-pressure flow stream from the pumps travels through the loop and pushes the sample out of the loop into the mobile phase flow stream. While inline, the volumetric space of the loop becomes pressurized with the mobile phase, which can range from 100 to 600 bar.

After the sample is injected, the valve is reset to a load position inline with a sample fill port 74. However, high-pressure mobile phase that was flowing through the loop becomes trapped in the sample loop. When the valve is reset to load, high-pressure mobile phase in the sample loop is brought inline with the fill line from the fill port and quickly expands in a 500:1 ratio into any low-pressure zones. This presents a serious safety hazard. Loops sizes for preparatory SFC may range from 0.1 to 20 mL, however larger loop sizes of up to 100 mL are also used. Mobile phase under pressure in an injection loop can rapidly expand from one-half up to 50 liters of mobile phase gasses and aerosols when exposed to atmospheric pressure. The expanding gas can exit an SFC system in an uncontrolled manner out of the fill port and into the open air. The reaction places the laboratory personnel and sensitive laboratory equipment at risk from exposure to decompressed mobile phase that contains hazardous substances.

A further hazard emanating from the expanding flow stream arises when laboratory personnel forget to remove a syringe from a previous injection from the fill port when the valve is reset to the load position. Syringes are used in SFC to manually fill the injection valve loop. Syringes are not always removed properly from a fill port after filling an injection loop. The pressure from trapped mobile phase in an injection valve loop from a previous injection can blow a syringe out of the sample fill port and propel the sharp projectile at high velocity through the laboratory, creating an obvious safety hazard to personnel and equipment.

The present invention minimizes the hazards of chemical exposure and physical projectiles associated with expansion of high-pressure mobile phase through an injection valve by moving the injection location to modifier flow stream location 22. The present invention removes the time-delays associated with dissipating pressures trapped in an injection valve and blow-back from an injection valve into a laboratory. Timing of injections are not slowed by further handling of dissipation of a pressure-charged injection valve.

Injecting into the low-pressure modifier stream 11 is an efficient method of adding sample to an SFC system. Dissipating high pressure trapped in an injection valve to a waste line also causes greater complication to the injection process resulting in time delays which slow the entire SFC process. Any pressure that is built up in the loop is dissipated to a waste system through a waste line port in the injection valve. This method allows the sample injection loop to reload for a subsequent filling of sample without additional handling or time delays for rapid repeated injections available in SFC. After dispensation of the mobile phase to a waste collector, samples may be rapidly added to the injection valve after an injection into the mobile phase.

Lower volumes of spent solvents are generated for disposal using the method of the preferred embodiment, which is good for the environment. Certain volumetric flow rates are maintained in SFC systems through the column 26. In analytical SFC, volumes of less than 0.1 mL of sample are injected, however in preparatory SFC and supercritical fluid extraction sample volumes of 0.1 to 100 mL are injected. As greater volumes of sample are added to the stream, less modifier is needed to maintain a constant flow rate since the sample offsets the modifier volume in the flow stream, thereby generating less spent solvent that must be disposed as waste. The present invention reduces a hazard not only to humans but also to the environment. The method eliminates uncontrolled expansion of mobile phase out of an injection valve and into the atmosphere as clouds of aerosols and gasses containing hazardous substances. The present invention improves the environment by minimizing the risk of exposure to high-pressure mobile phase flow stream mixtures expanding into the open air atmosphere. The mobile phase can contain other hazardous substances such as hexane, acetonitrile, and freon, which can also escape from the system.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed:

1. An apparatus for sample introduction into a high-pressure chromatography system, comprising:
    a first flow stream comprising a mixture of highly compressed gas, compressible liquid, or supercritical fluid;
    a second flow stream comprising a relatively incompressible liquid;
    a sample injection valve located in said second flow stream downstream of a first flow stream pump and upstream of a mixing point of said first flow stream and said second flow stream;
    a chromatography column located downstream of said mixing point of said first flow stream and said second flow stream;
    said flow streams combining into a mobile phase that is compositionally controlled through adjustments of the ratios of said flow streams and injection of sample through said injection valve, thereby controlling focusing of sample components onto said column.

2. The apparatus of claim 1, wherein:
    said flow stream of relatively incompressible liquid is modifier solvent.

3. The apparatus of claim 1, further comprising:
    means for controlling the composition of the mobile phase at a column injection point during injection to cause greater or lesser focusing of components by changing the ratio of said first flow stream to said second flow stream.

4. The apparatus of claim 1, wherein:
    said injection valve is a multi-port injection valve with a microliter flow loop.

5. The apparatus of claim 1, wherein:
    means decreasing the time of sample separation in a column by artificially increasing composition of said second flow stream for some period.

6. The apparatus of claim 1, wherein:
    means for adjusting total flow rate of said mobile phase to speed the application of the sample onto the column after injection.

7. The apparatus of claim 1, wherein:
    means for reducing the amount of modifier needed to maintain a constant flow rate in proportion to the amount of sample added to the system.

8. An apparatus for sample introduction onto a chromatography column receiving a high-pressured mobile phase flow stream that is a confluence of two separate flow streams, comprising:
    a first flow stream comprised of a mixture of highly compressed gas, compressible liquid or supercritical fluid;
    a second flow stream comprising a relatively incompressible liquid;
    means for injecting a sample into said second flow stream with a single injection valve between a pumping stage of said second flow stream and a mixing point of said first flow stream with said second flow stream.

9. The apparatus of claim 8, wherein:
    said flow stream of relatively incompressible liquid is modifier solvent.

10. The apparatus of claim 8, further comprising:
    means for adjusting the composition of the mobile phase at a column injection point during sample injection to cause greater or lesser focusing of components by changing the ratio of said first flow stream to said second flow stream.

11. The apparatus of claim 8, further comprising:
    means for injecting a sample into said second flow stream comprises injecting sample from a sample loop on said injection valve into said second flow stream.

12. The apparatus of claim 8, further comprising:
    means for decreasing the time of sample separation in a column is decreased by artificially increasing composition of said second flow stream for some period.

13. The apparatus of claim 8, further comprising:
    means for controlling compositional changes of said mobile phase flow stream during an injection period resulting in improved sample analysis and production.

14. The apparatus of claim 8, further comprising:
    means for adjusting the total flow rate to speed the application of the sample onto the column after injection.

15. The apparatus of claim 8, further comprising:
    means for reducing the amount of said modifier needed to maintain a constant flow rate in proportion to the amount of said sample added to the system.

* * * * *

UNITED STATES PATENT AND TRADEMARK OFFICE
CERTIFICATE OF CORRECTION

PATENT NO. : 6,576,125 B2
APPLICATION NO. : 09/931238
DATED : June 10, 2003
INVENTOR(S) : Terry A. Berger and Kimber D. Fogelman It is certified that error appears in the above-identified patent and that said Letters Patent is hereby corrected as shown below:

In the Claims:

Column 7, in Claim 1, line 30, "first flow stream pump" should read --second flow stream pump--

Signed and Sealed this
Ninth Day of July, 2013

Teresa Stanek Rea
*Acting Director of the United States Patent and Trademark Office*